United States Patent [19]

Bornhoeft, III et al.

[11] Patent Number: 5,049,440

[45] Date of Patent: Sep. 17, 1991

[54] WET WIPER NATURAL ACID AND SALT PRESERVATIVE COMPOSITION

[75] Inventors: John W. Bornhoeft, III, Wilmette, Ill.; Jerry R. Nelson, Salt Lake City, Utah

[73] Assignee: The James River Corporation, Richmond, Va.

[21] Appl. No.: 388,068

[22] Filed: Jul. 28, 1989

[51] Int. Cl.$^5$ .................. A61F 13/00; A61K 9/70; D06M 13/192

[52] U.S. Cl. .................. 428/288; 15/104.93; 15/209 R; 206/210; 206/812; 424/404; 428/74; 428/289; 604/360

[58] Field of Search .................. 15/104.93, 209 R; 206/210, 812; 424/404; 428/74, 288, 289; 604/360

[56] References Cited

U.S. PATENT DOCUMENTS

| | | | |
|---|---|---|---|
| 2,689,809 | 9/1954 | Fessler | 424/404 |
| 4,220,224 | 9/1980 | Elmore | 206/210 |
| 4,467,013 | 8/1984 | Baldwin | 428/288 |
| 4,615,937 | 10/1986 | Bouchette | 428/288 |
| 4,678,698 | 7/1987 | Mencke | 428/288 |
| 4,692,374 | 9/1987 | Bouchette | 428/288 |
| 4,732,797 | 3/1988 | Johnson et al. | 428/74 |
| 4,737,405 | 4/1988 | Bouchette | 428/288 |
| 4,740,398 | 4/1988 | Bouchette | 428/288 |
| 4,772,492 | 9/1988 | Bouchette | 427/342 |
| 4,772,501 | 9/1988 | Johnson et al. | 428/74 |
| 4,781,974 | 11/1988 | Bouchette | 428/288 |
| 4,975,217 | 12/1990 | Brown-Skrobot | 424/404 |

OTHER PUBLICATIONS

J. Curry, "Water Activity and Preservation", 100 Cosmetics & Toiletries 53-54 (Feb. 1985).

*Primary Examiner*—James C. Cannon
*Attorney, Agent, or Firm*—Finnegan, Henderson Farabow, Garrett & Dunner

[57] ABSTRACT

An antimicrobially active wet wiper product having a fibrous wipe and a hypotonic liquid preservative composition for the wipe. The liquid preservative composition comprises: (i) water, (ii) a naturally occurring organic acid in an amount effective to be a preservative, and (iii) a naturally occurring salt in a concentration effective to increase the efficacy of the naturally occurring organic acid.

20 Claims, No Drawings

WET WIPER NATURAL ACID AND SALT PRESERVATIVE COMPOSITION

BACKGROUND OF THE INVENTION

The present invention relates to wet wiper products and, more particularly, to a wet wiper product having a liquid preservative composition of both a naturally occurring acid and a naturally occurring salt.

Wet wiper products require preservative properties to destroy or inhibit the growth of various microorganisms, bacteria, yeast, and molds. The use of a chemical preservative agent dispersed or dissolved in a liquid phase of a wet wiper has previously met various disadvantages because the nature of the required chemicals and the complexity of the final liquid phase formulations typically result in harsh or irritating residues being left behind on the skin of the user.

The preservative used in a wet wiper should meet two often competing criteria, namely effectiveness as a preservative and non-irritability in contact with human skin. As resistant strains to commonly utilized preservatives appear, the industry has typically increased usage levels and the number of preservative components in the wet wiper. As more potent strains of preservatives are utilized to achieve the desired effect, skin irritations and allergic reactions are often provoked in the user.

In an attempt to solve these problems, U.S. Pat. Nos. 4,615,937 and 4,692,374 to Michael P. Bouchette discloses that a superior wet wiper product can be produced in which the antimicrobial treatment is substantive to the wet wiper fibers. As a result of having the antimicrobial agent substantive to the fibers, no chemicals in the liquid or lotion phase of the wiper are required As a further improvement, U.S. Pat. No. 4,781,974 to Bouchette et al. discloses a wet wiper that has both a substantive antimicrobial agent on the fibers of the wet wiper product and a second antimicrobial agent, such as an organic acid, in the liquid or lotion phase of the wiper. Moreover, U.S. Pat. Nos. 4,732,797 and 4,772,501 to Johnson et al. discloses a wet wiper product that maintains a fibrous wipe in a liquid preservative composition that consists essentially of a mixture of citric acid and sorbic acid, water, and optional ingredients such as skin moisturizers and fragrance compounds. This wet wiper does not leave a harsh or irritating residue on the user's skin.

SUMMARY OF THE INVENTION

The present invention improves upon these previous wet wiper products and achieves various advantages by providing a wet wiper product that comprises a fibrous wipe and a hypotonic liquid preservative composition for the wipe. The liquid preservative composition comprises: (i) water, (ii) a naturally occurring organic acid in an amount effective to be a preservative, and (iii) a naturally occurring salt in an amount effective to increase the efficacy of the naturally occurring organic acid.

The present inventors have discovered that such a liquid preservative composition could improve a wet wiper product that contains a naturally occurring acid, such as sorbic acid and citric acid, in the liquid preservative composition without any salt. It has been found that the addition of a naturally occurring salt, such as sodium chloride, to the liquid preservative composition can increase the efficacy, as well as the antimicrobial spectrum, of the naturally occurring acid.

Thus, the wet wipe product of the present invention has an effective liquid preservative composition that has all naturally occurring components, namely the naturally occurring acid and the naturally occurring salt. The wet wiper product exhibits the requisite preservative functions without the need for any other preservative agents, especially a non-naturally occurring agent, in the preservative composition. Importantly, the present invention provides the advantage of not being irritating or harsh to the skin.

These and other features of the present invention will be made more apparent from the following description of the preferred embodiments.

DESCRIPTION OF THE PREFERRED EMBODIMENTS

In accordance with the present invention, the wet wiper product comprises a fibrous wipe and a liquid preservative composition for the wipe. For this discussion of fibrous wipes and liquid preservative compositions, U.S. Pat. Nos. 4,732,797 and 4,772,501 to Johnson et al. are hereby incorporated by reference.

The fibrous wipe can be selected from those conventionally known in the art. Preferably, the fibrous wiper is a non-woven web that comprises bonded fibers and a binder in an amount effective to bind the fibers. The non-woven web can be antimicrobial. Such a web is disclosed in U.S. Pat. No. 4,692,374.

Various synthetic and natural fibers known in the art can be effectively used. Preferred fibers are cellulosic fibers and, more preferably, wood pulp fibers. The cellulosic fibers, such as wood pulp fibers, can be chemically treated prior to the formation of the web or fabric, if desired. Examples of wood pulp fibers include various mechanical and chemical pulp fibers, such as cedar fibers, southern pine fibers, spruce fibers, and hemlock fibers. The particular fibers may be specifically selected to enhance properties such as texture (soft, wooly or fluffy), porosity, caliper, brightness, and strength. Alternatively, the fibers can be a combination of natural and synthetic fibers, or synthetic fibers alone, depending upon the final attributes sought and the method of forming the web.

The weight of the fibers, such as cellulosic fibers, used to form the unbonded fibrous web can vary depending upon the ultimate non-woven web that is produced. Typically, the weight of the fibers forming the web will vary within the range of about 5 lbs. per 3000 $ft^2$ to about 60 lbs. per 3000 $ft^2$.

Various web or fabric forming techniques known in the art can be effectively used to form the unbonded fibers. The web can be formed by nonwoven techniques, such as air-laying or wet-laying the web. One type of apparatus for air forming fibers is shown in U.S Pat. No. 4,292,271 to Buob et al. Other nonwoven manufacturing techniques, such as melt blown, spunbonded, needle punched, and spun laced, may also be used.

Various binders known in the art can be used to bind the fibers together. A preferred binder is a polymeric binder, such as a latex binder. Acceptable latex binders include acrylate emulsions, butadiene-styrene emulsions, ethylene vinyl acetate emulsions and acrylonitrile-butadiene emulsions. An especially effective latex binder is ethylene vinyl acetate, which is sold under the trademark AIRFLEX A-410 by Air Products, Inc. of Allentown, Pa. The binder can also include a mixture of anionic and nonionic binders, such as an ethylene vinyl acetate binder sold under the trademark AIRFLEX A-106 by Air Products, Inc. and an ethylene acetate binder sold under the trademark HA-8 by Rohm & Haas of Philadelphia, Pa.

The amount of the binder that is to be applied to the fibers depends, in part, upon the type of fibers, such as cellulosic. Typically, the amount of the binder applied to the fibers varies within the range of about 5% to about 30% of the total web weight. Similarly, the amount of solids in the binder, as applied to the web, especially in a latex binder, depends, among other things, on the weight of the fibers in the nonwoven web. Generally, latex binders having from about 5% to about 25% application solids content are used. Of course, one of ordinary skill in the art can select the particular binder, the amount of the binder used, and the amount of solids present in the binder, depending upon, in part, the type of fibers that are to be bound. The binder is applied to the fibers by various techniques known in the art, such as spraying, foaming, or padding.

In accordance with the present invention, the wet wiper product has a hyptonic liquid preservative composition comprising: (i) water, (ii) a naturally occurring acid in an amount effective to be a preservative, and (iii) a naturally occurring salt in an amount effective to increase the efficacy of the naturally occurring organic acid. The liquid preservative composition acts as an antimicrobial to preserve and prevent microbial contamination of the fibrous wipe until it can be used. In addition to increasing the efficacy of the organic acid, the salt can also increase the antimicrobial spectrum of the acid so that the acid is effective against a wider range of microorganisms.

The present invention achieves the desired properties in a wet wiper with only a naturally occurring acid as the preservative component without the need for any other preservative component, such as an antimicrobial agent, in the wet wiper. This can be achieved since the naturally occurring salt enhances this antimicrobial effect of the naturally occurring acid.

The naturally occurring acid is preferably selected from the group consisting of citric acid, sorbic acid, malic acid, tartaric acid, benzoic acid, and mixtures thereof. Of course, other naturally occurring acids may be used so long as they provide the requisite preservative effect without being harsh or irritating to the skin of the user. The naturally occurring acid is preferably present in a concentration within the range of about 0.1 w/v % to about 0.7 w/v % based upon the liquid preservative composition.

Preferably, the naturally occurring acid comprises a mixture of sorbic acid and citric acid and, most preferably, a mixture in an amount of about 0.01 w/v % to about 0.2 w/v % sorbic acid and about 0.1 w/v % to about 0.5 w/v % citric acid based upon the liquid preservative composition. An especially effective naturally occurring acid is a mixture of 0.05 w/v % to about 0.10 w/v % sorbic acid and 0.3 w/v % to about 0.5 w/v % citric acid. The weight ratio of citric acid to sorbic acid in the liquid preservative composition is preferably in the range of about 20 to 1 to about 1 to 1, and, most preferably, in the range of about 10 to 1 to about 3 to 1.

Citric acid (2-hydroxy-1,2,3-propanetricarboxylic acid) and sorbic acid (2,4-hexadienoic acid) are mild, naturally occurring organic acids that are relatively safe for skin contact and are edible. Consequently, users of the wet wiper typically do not exhibit adverse reactions to the wet wiper, even under repeated occlusive applications to human skin under conditions in which conventionally preserved products exhibit some irritation.

The pH of the liquid preservative composition is preferably below about 3.5. More preferably, the liquid preservative composition has a pH in the range of about 2.0 to about 3.2. Such a pH range for a wet wiper does not necessarily result in extensive skin or eye irritation when a naturally occurring acid, such as sorbic acid and citric acid, are the only preservative components. Any such skin and eye irritation that may occur is especially minimized in the present invention because the acid, such as citric acid and sorbic acid, are relatively nonirritating substances.

The combination of citric acid and sorbic acid in the liquid preservation composition provides excellent preservative activity against various microorganisms, particularly the five pathogenic microorganisms identified in the U.S.P. XXI Antimicrobial Preservatives-Effectiveness twenty-eight day challenge test: *Aspergilua niger, Candida albicans, Staphylococcus aureus, Pseudomonas aeruginosa,* and *Escherichia coli*. Neither component alone demonstrates the breadth of kill spectrum or speed as the combination of the citric and sorbic acids.

The naturally occurring salt in the preservative composition is present in a concentration effective to increase the efficacy of the naturally occurring organic acid. Preferably, the salt also incrases the antimicrobial spectrum of the acid. Preferably, the naturally occurring salt is selected from the group consisting of monobasic or dibasic sodium phosphate, potassium chloride, sodium chloride, and mixtures thereof. The naturally occurring salt is preferably present in a concentration of about 0.1 w/v % to about 0.9 w/v % based upon the liquid preservative composition. Sodium chloride is the preferred natural salt and is preferably prsent in an amount of 0.1 w/v % to 0.5 w/v %.

The liquid preservative composition is hypotonic, which property is believed to increase the efficacy and antimicrobial spectrum of the natural acid preservative composition. To determine whther the liquid preservative composition is hypotonic, its osmotic pressure after the addition of the naturally occurring salt is to be compared to a 0.9% w/v physiological saline having an osmotic pressure of 286 milli-osmole/kg. If after the addition of the salt the osmotic pressure of the composition is lower, than that of the saline solution, it is hypotonic. The osmotic pressure of the preservative composition is preferably within the range of about 110 milli-osmole/kg to about 280 milli-osmole/kg to render the composition hypotonic.

Solutions with high osmotic pressure (hypertonic) have historically been used for food preservation (pickling in brine), since most microorganisms are killed by high salt concentrations. The present invention, however, is the first use of a hypotonic salt solution to improve the efficacy and antimicrobial spectrum of a wet wiper natural acid preservative system. A hypotonic solution, as demonstrated in the medical literature, is non-irritating to the skin and eyes when compared to hypertonic solutions. Without being bound by theory, it is believed that the sorbic acid and citric acid as the natural acid preservative inhibits and/or kills microorganisms by (i) causing leakage of hydrogen ions across the cell membrane, (ii) acidifying the cell interior, and (iii) inhibiting nutrient transport. The salt may aid in this action and therefore increase the efficacy of the preservative system; and/or the effect of the acid combination may allow salt ions to enter the cell and interfer with cellular functions; and/or it is simply the osmotic effect of the salt.

The osmotic pressure of the natural acid preservative composition can be adjusted by the addition of the naturally occurring salt in an amount sufficient to cause the osmotic pressure to be within the desired range.

The liquid preservative composition in the present invention also includes water and can include optional ingredients selected from the group consisting of skin moisturizers and fragrance compounds. Pure water that is safe for skin contact is preferred. The liquid preservative composition need not include any skin moisturizers or fragrance compounds since these are optional ingredients. The wt. % total of the preservative component, water and the optional ingredients is 100 wt. %.

The skin moisturizers can be selected from various moisturizers well known in the art, such as glycerine, aloe vera, lecithin, lanolin and lanolin derivatives. Other skin moisturizers known in the art can also be readily used in amounts known in the art to achieve the intended purpose of moisturizing the skin upon use. In one embodiment, an effective amount of aloe vera could be used as a skin moisturizer.

Similarly, fragrance compounds, such as water soluble fragrance compounds, can be used. Such fragrance compounds are well known and conventionally used in the art. For example, fragrance compounds can be readily obtained from International Food and Flavor, Inc. (I.F.F.). The proper fragrance compound can be selected by one skilled in the art without undue experimentation.

A means can be used to enclose the fibrous wipe in the liquid preservative composition. In one embodiment of the present invention, the enclosure means for the fibrous wipe is a sealed package or sealed envelope, of the type conventionally used in the art, to enclose the fibrous wipe in the liquid preservative composition until the time of use. The fibrous wipe and the preservative composition can be sealed within the enclosure by various techniques well known in the art. Other enclosure means well known in the art can also be used.

In one embodiment of the present invention, the wet wiper product comprises: (1) a latex bonded, cellulosic fiber wipe, (2) a liquid preservative composition consisting essentially of (i) 0.4 w/v % citric acid and 0.05 w/v % sorbic acid, (ii) 0.5 w/v % sodium chloride, and (iii) water to 100 wt. %; and (3) an outer sealed package enclosing the wet wipe to maintain the wet wipe in the liquid preservative composition until use. The wet wipe also can include, as noted, an effective amount of a moisturizer, such as aloe vera, and an effective amount of a fragrance compound.

The following are examples of the present invention and are intended to be merely exemplary.

EXAMPLES

Example No. 1

A wet wiper product was prepared. The product comprised: (1) a latex bonded cellulosic fiber wipe and (2) a liquid preservative composition consisting essentially of 0.105 w/v % sorbic acid, 0.375 w/v % citric acid, 0.005 v/v % of a moisturizer, and 0.22 v/v % of a fragrance, and water to 100 wt. %. This wet wiper without a naturally occurring salt in the preservative composition was compared to wet wipers that were the same but for the inclusion of also a naturally occurring salt in the preservative composition.

The primary microorganism used to test for antimicrobial efficacy was an *Acetobacter aceti* bacterium isolated from the environment and identified by the American Type Culture Collection (ATCC). The antimicrobial effect was tested using a modified minimum lethal concentration (MLC) protocal as described in the *Manual of Clinical Microbiolgy* (3d ED), published by the American Society for Microbiology. The total test period was 6 hours. Incubation was performed at room temperature.

The test results presented in Tables IA, IB, and IC show the increased efficacy of a preservative composition having a naturally occurring acid and a naturally occurring salt in comparison to a preservative composition having a naturally occurring acid, but no naturally occurring salt.

TABLE I - A

MLC Comparison of the Wet Wiper Natural Acid Preservation System with and without Added Sodium Chloride

| Sample Identification | Osmotic Pressure | Results Percent Reduction in Bacterial Colony Forming units (cfu) Sample (Incubation) Period | | | |
|---|---|---|---|---|---|
| | | 1 hour | 2 hours | 4 hours | 6 hours |
| Wet Wiper Natural Acid Preservative System. | | | | | |
| Tested at 75% concentration | 21 mOs/kg | 40.6 | 51.7 | 49.0 | 69.9 |
| Tested at 50% concentration | | (18.8) | 21.6 | 41.0 | 30.0 |
| Wet Wiper Natural Acid Preservative System with 0.5% Sodium chloride. | | | | | |
| Tested at 75% concentration | 149 mOs/kg | 99.9 | 99.994 | >99.999 | >99.999 |
| Tested at 50% concentration | | 37.2 | 91.0 | 99.6 | >99.999 |

( ) = Bacterial growth

Challenge Organism = *Acetobacter aceti*

TABLE I - B

MLC Comparison of the Wet Wiper Natural Acid Preservation System with and without Added Sodium Chloride

| | Results Percent Reduction in Bacterial Colony Forming units (cfu) Sample Dilution Factor | | | |
|---|---|---|---|---|
| Sample Identification | 1:2 | 1:4 | 1:8 | 1:16 |
| Wet Wiper Natural Acid Preservative System. | 99.92 | 99.92 | 99.96 | 97.8 |
| Wet Wiper Natural Acid Preservative System with | | | | |
| (a) 0.5% Sodium Chloride added | >99.999 | >99.999 | >99.999 | 95.7 |
| OR | | | | |
| (b) 0.75% Sodium Chloride added | >99.999 | >99.999 | >99.999 | 98.3 |

Challenge Organism = *Acetobacter aceti*
The MIC incubation period was 24 hours at room temperature.

TABLE I - C

MLC Comparison of the Wet Wiper Natural Acid Preservation System with and without Added Sodium Chloride

| | | Results Percent Reduction in Bacterial Colony Forming units (cfu) Sample (Incubation) Period | | | | |
|---|---|---|---|---|---|---|
| Sample Identification | Osmolarity | 1 hour | 2 hours | 4 hours | 6 hours | 8 hours |
| Wet Wiper Natural Acid Preservative System. Tested at 75% concentration | 30 mOs/kg | (51.1) | 57.8 | 60.7 | 93.6 | 99.7 |
| Wet Wiper Natural Acid Preservative System with 0.5% Sodium chloride added. Tested at 75% concentration. | 146 mOs/kg | 42.8 | >99.999 | >99.999 | >99.999 | >99.999 |

( ) = Bacterial growth
Challenge Organism = *Acetobacter aceti*
The total test period was 8 hours.
Incubation was performed at room temperature.

Example No. 2

The test results shown in Table IIA and IIB demonstrate the increased efficacy of the present preservative composition having both a naturally occurring acid and salt compared to a preservative composition having only the salt when the preservative composition is used with an antimicrobiallly active, nonwoven web as described in U.S. Pat. Nos. 4,692,374 and 4,772,501.

TABLE II - A

28-Day Fabric Challenge Test on an Antimicrobially Active Nonwoven Fabric Saturated with a Natural Acid Preservation System with and without Added Sodium Chloride

| Sample Identification Antimicrobially Active Nonwoven Fabric | Results Percent Reduction in Bacterial Colony Forming Units (cfu) Sample (Incubation) Period | | | | | | | | | | |
|---|---|---|---|---|---|---|---|---|---|---|---|
| | 1 hour | 2 hours | 4 hours | 8 hours | 1 day | 2 days | 4 days | 7 days | 14 days | 21 days | 28 days |
| a. Saturated with a Natural Acid Preservation System | (16.3) | 19.6 | 21.8 | 53.7 | 57.9 | (54.2) | 32.2 | 81.9 | 81.0 | >99.999 | >99.999 |
| b. Saturated with a Natural Acid Preservation System with 0.75% Sodium Chloride Added | 35 | 52.6 | 61.4 | 74.4 | 90.2 | 97.6 | 99.92 | >99.999 | >99.999 | >99.999 | >99.999 |

( ) = Bacterial growth
Challenge Organism = *Acetobacter aceti*
Procedure: Modified USP XXI Antimicrobial Preservatives-Effectiveness Test

TABLE II - B

56-Day in Tub Fabric Challenge Test on an Antimicrobially Active Nonwoven Fabric Saturated with a Natural Acid Preservation System with and without Added Sodium Chloride

| Sample Identification Antimicrobially Active Nonwoven Fabric | Results Percent Reduction in Bacterial Colony Forming Units (cfu) Sample (Incubation) Period | | | | | |
|---|---|---|---|---|---|---|
| | 4 days | 7 days | 14 days | 21 days | 28 days | 56 days |
| a. Saturated with a Natural Acid Preservation System | 99.9 | 83.4 | 41.3 | 37.9 | 10.3 | 89.1 |

TABLE II - B-continued

56-Day in Tub Fabric Challenge Test on an Antimicrobially Active Nonwoven Fabric Saturated with a Natural Acid Preservation System with and without Added Sodium Chloride

| Sample Identification Antimicrobially Active Nonwoven Fabric | Results Percent Reduction in Bacterial Colony Forming Units (cfu) Sample (Incubation) Period | | | | | |
|---|---|---|---|---|---|---|
| | 4 days | 7 days | 14 days | 21 days | 28 days | 56 days |
| b. Saturated with a Natural Acid Preservation System with 0.5% Sodium Chloride Added | 99.97 | >99.999 | >99.999 | >99.999 | >99.999 | >99.999 |

Challenge Organism = *Acetobacter aceti*
Procedure: Modified USP XXI Antimicrobial Preservatives-Effectiveness Test

Example No. 3

A preservative composition containing a naturally occurring acid was compared to the same preservative compositions that also contained 0.5 w/v sodium chloride, 0.5 w/v sodium phosphate (monobasic), or 0.5 w/v potassium sorbate. Each sample was diluted to a 75%, a 50%, and a 25% concentration. These sample concentrations were then inoculated with *Acetobacter aceti* at a concentration of $7.55 \times 10^5$ and incubated at 70° F. for various time periods. The bacterial colony forming units (CFU) were enumerated at 0 time, 1 hour, 2 hours, 4 hours, and 6 hours and the percent reductions were then calculated. The osmolarity of each sample and 0.9% saline at the 75% concentration was also determined. The results are shown in Table III.

The results for the four test samples demonstrate that the preservative composition containing 0.5 w/v sodium chloride exhibited the best preservative properties and the preservative composition having 0.5 w/v potassium sorbate exhibited the second best preservative properties. Without being bound by theory, it is believed that the potassium sorbate acts as a biocide as well as serving to raise the osmotic pressure of the preservative compositions.

Example No. 4

A liquid preservative composition not containing a naturally occurring organic salt (Sample No 1 at 75% concentration and 30 mOs/kg) was compared with sample Nos 2-6 of the same preservative composition plus the designated naturally occurring organic salt Example No. 7 was plain water.

| Sample No. | Salt | Osmolarity mOs/kg |
|---|---|---|

TABLE III

Summary of Experimental Results:

| Sample | Concentration 75% | 50% | 25% | mOs/Kg 75% Concentration |
|---|---|---|---|---|
| Liquid Load (LL) | An initial cfu % reduction of 40.6% was observed at 1 hour and within 6 hours at 69.9% reduction was achieved. | Initially bacterial growth was demonstrated. Thsi growth was followed by a modest cfu reduction with indications of a bacterial regrowth apparent at 6 hours | This concentration demonstrated a growth, reduction regrowth pattern similar to the 50% concentration. | 21 |
| LL + 0.5% Sodium Chloride | A greater than 99.9% cfu reduction was observed at all time periods. | An initial cfu reduction was observed within 1 hour and was greater than 99.9% at the 4 hour and 6 hour sampling periods.1 | Initially bacterial growth was observed, by at the 6 hour sampling period a 34% cfu reduction was observed. | 149 |
| LL + 0.5% Sodium Phospate | At all concentrations initial bacterial growth was observed. At the 6 hour sampling period, however, all concentrations demonstrated a modest reduction in bacterial cfu isolates. At the 25% concentration there was indication of a bacterial regrowth at the 6 hour sampling period. | | | 73 |
| LL + 0.5% Potassium Sorbate | A steady decrease in cfu recoveries was demonstrated. At the 6 hour sampling period the % reduction was 99.0%. | Initial growth, followed by a decrease in cfu recoveries was observed. (The 4 hour cfu recoveries appear to be an unexplained laboratory anomoly). The % reduction at the 6 hour sampling period was 63.7%.1 | Initially growth occured. This growth was followed by a modest reduction in cfu recoveries at the 2, 4 and 6 hour sampling periods. There was, however, an indication of bacterial regrowth at the 6 hour period. | 55 |
| 0.9% Saline | — | | | 149 |
| Challenge Organism | The challenge organism survived throughout all time periods. Initially, at 1 hour, growth was observed. During the subsequent time periods, a modest reduction in cfu was reported. This modest reduction was consistent with previous studies on *Acetobacter aceti* | | | 0 |

| | | |
|---|---|---|
| 2 | 0.5% sodium chloride | 146 |
| 3 | 0.5% potassium sorbate | 75 |
| 4 | 0.7% potassium sorbate | 93 |

-continued

| Sample No. | Salt | Osmolarity mOs/kg |
|---|---|---|
| 5 | 0.9% potassium sorbate | 115 |
| 6 | 1.0% potassium sorbate | 130 |
| 7 | Water | 0 |

Each sample was inoculated with *Acetobacter aceti* and incubated for 8 hours at 72° F. Aliquotes of the test samples were analyzed for CFU recoveries at 0 minutes, 1 hour, 2 hours, 4 hours, 6 hours and 8 hours. The bacterial CFUs were enumerated using standard microbiological technologies. The test results are shown in Table IV.

Example No. 5

A 28 day fabric challenge test was performed with the following samples:

| Sample No. | Description | Osmolarity (mOs/kg) |
|---|---|---|
| 1 | 0.75% saline on bioweb + pres. comp. | 268 |
| 2 | 0.75% saline on non-bioweb + pres. comp. | 290 |
| 3 | Control | 105 |
| 4 | Pres. comp. without saline on bioweb | 125 |
| 5 | Cotton control - 100% cotton | |

Pres. comp. denotes a liquid preservative composition. Results of the test are shown in Table V.

TABLE IV

MODIFIED MLC
Challenge Organism = *Acetobacter aceti*

| INTERVAL | .75% LIQUID LOAD | .5% NACL LIQUID LOAD | .5% SORB LIQUID LOAD | .7% SORB LIQUID LOAD | .9% SORB LIQUID LOAD | 1.0% SORB LIQUID LOAD | WATER CONTROL |
|---|---|---|---|---|---|---|---|
| 0 HOUR AVERAGE CFU % REDUCTION (INCREASE) | 354511 | 372667 | 838889 | 885556 | 877778 | 821111 | 798889 |
| 1 HOUR AVERAGE CFU % REDUCTION (INCREASE) | 535556 (51.1) | 213337 42.8 | 379333 54.8 | 557778 37.0 | 434444 50.5 | 526667 35.9 | 463333 42.0 |
| 2 HOURS AVERAGE CFU % REDUCTION (INCREASE) | 149667 57.8 | 0 >99.9999 | 310889 62.9 | 443333 49.9 | 158778 81.9 | 257556 68.6 | 326667 59.1 |
| 4 HOURS AVERAGE CFU % REDUCTION (INCREASE) | 139222 60.7 | 0 >99.9999 | 179222 78.6 | 295889 66.6 | 322889 63.2 | 313211 61.9 | 348778 56.3 |
| 6 HOURS AVERAGE CFU % REDUCTION (INCREASE) | 22711 93.6 | 0 >99.9999 | 88778 89.4 | 118333 86.6 | 121556 86.2 | 175778 78.6 | 368000 53.9 |
| 8 HOURS AVERAGE CFU % REDUCTION (INCREASE) | 1078 99.7 | 0 >99.9999 | 29278 96.5 | 62111 93.0 | 38011 95.7 | 66667 91.9 | 564444 29.3 |

As shown in the table, at the end of the 8 hour test period, Sample No. 1 had reduced the CFU by 99.7%. Sample No. 2 had a 99.999% reduction in CFU recoveries within 2 hours after the initial innoculation.

TABLE V

*Acetobacter aceti*

| INTERVAL | 1 | 2 | 3 | 4 | COTTON CONTROL 5 | CHALLENGE CONTROL 6 |
|---|---|---|---|---|---|---|
| 0 HOUR AVERAGE CFU % REDUCTION (INCREASE) | 2381 | 2016 | 3091 | 1666 | 1586 | 29800 |
| 1 HOUR AVERAGE CFU % REDUCTION (INCREASE) | 1538 35.4 | 5 99.8 | 1840 40.5 | 1938 (16.3) | 3656 (130.5) | 21644 27.4 |
| 2 HOURS AVERAGE CFU % REDUCTION (INCREASE) | 1129 52.6 | 0 >99.99 | 1036 66.5 | 1340 19.6 | 1606 (1.3) | 17671 40.7 |
| 4 HOURS AVERAGE CFU % REDUCTION (INCREASE) | 919 61.4 | 0 >99.99 | 1076 65.2 | 1303 21.8 | 1781 (12.3) | 56556 (89.8) |
| 8 HOURS AVERAGE CFU % REDUCTION | 610 74.4 | 0 >99.99 | 309 90.0 | 772 53.7 | 3184 (100.8) | 16544 44.5 |

TABLE V-continued

| | Acetobacter aceti | | | | COTTON CONTROL | CHALLENGE CONTROL |
|---|---|---|---|---|---|---|
| INTERVAL | 1 | 2 | 3 | 4 | 5 | 6 |
| (INCREASE) 24 HOURS | | | | | | |
| AVERAGE CFU | 234 | 0 | 28 | 701 | 72111 | 58778 |
| % REDUCTION (INCREASE) | 90.2 | >99.99 | 99.1 | 57.9 | (4,446.7) | (97.2) |
| 48 HOURS | | | | | | |
| AVERAGE CFU | 58 | 0 | 554 | 2569 | 188000 | 124444 |
| % REDUCTION (INCREASE) | 97.6 | >99.99 | 82.1 | (54.2) | (11,753.7) | (317.6) |
| 96 HOURS | | | | | | |
| AVERAGE CFU | 2 | 0 | 609 | 1130 | 16333 | 161556 |
| % REDUCTION (INCREASE) | 99.92 | >99.99 | 80.3 | 32.2 | (929.8) | (442.1) |
| 7 DAYS | | | | | | |
| AVERAGE CFU | 0 | 0 | 699 | 301 | 8191 | 28756 |
| % REDUCTION (INCREASE) | >99.99 | >99.99 | 77.4 | 81.9 | (416.5) | 3.5 |
| 14 DAYS | | | | | | |
| AVERAGE CFU | 0 | 0 | 165 | 317 | 223844 | 41433 |
| % REDUCTION (INCREASE) | >99.99 | >99.99 | 94.7 | 81.0 | (14,013.7) | (39.0) |
| 21 DAYS | | | | | | |
| AVERAGE CFU | 0 | 0 | 829 | 0# | 1648 | 36933 |
| % REDUCTION (INCREASE) | >99.99 | >99.99 | 73.2 | >99.99 | (3.9) | (23.9) |
| 28 DAYS | | | | | | |
| AVERAGE CFU | 0 | 0 | 1181 | 0 | 40000 | 62333 |
| % REDUCTION (INCREASE) | >99.99 | >99.99 | 61.8 | >99.99 | (2,422.1) | (109.2) |

Note:
The CFU counts recorded in Table V are 1/300 of the actual CFU counts as a result of various dilutions. To obtain the actual CFU counts, the recorded CFU values in Table V should be multiplied by a factor of 300.

The results of the 28 day fabric challenge tests can be summarized as follows:

| Sample No. | Results |
|---|---|
| 1 | Organism reduced 99.92% on 96 hr. sample and reduced by greater than 99.999% on all successive samples. |
| 2 | Within 2 hrs. after innoculation, organism was reduced by greater than 99.999%. All successive samples were reduced by the same percentage for the full 28 day period. |
| 3 | The organism was isolated in significant numbers of CFU at all time periods sampled. |
| 4 | The organism was isolated in significant numbers of CFU through the 14 day sampling period. A greater than 99.999% CFU reduction was observed at the 21 and 28 day sampling periods. |
| 5 | Exhibited bacterial growth and survival for the full 28 day period. |

Thus, the use of 0.75% saline in Sample Nos. 1 and 2 increased the efficacy of the laboratory prepared bioweb and preservative composition.

Example No. 6

A 56 day tub challenge test was performed on the following test samples against *Acetobacter aceti* and *Aspergillus niger*.

| Sample No. | Description |
|---|---|
| 1 | Wet wipe with 0.5% sodium chloride added to liquid preservative composition. |
| 2 | Non-bioweb with 0.5% sodium chloride added to liquid. |
| 3 | Control - bioweb with liquid preservative without sodium chloride. |

Each sample tub was inoculated with the appropriate test organism near the top of the tub and near the bottom of the tub. The inoculated wipes were then segregated from the uninnoculated wipes with a layer of Saran Wrap ® located one towel below the inoculated towel and one towelette above the inoculated towel. The results of the test can be summarized as follows.

TABLE VI

Summary of Experimental Results:

| Test Sample | Organism | Top of Tub | Bottom of Tub |
|---|---|---|---|
| 1 | Acetobacter aceti | CFU recovered on day 4 but not on day 7 or thereafter. | No CFU recoveries at/ or after 4 days. |
| | A. niger | CFU not recovered on days 4, 7 and 56. A. niger, however was recovered on days 14, 21 and 28. | Identical CFU recovery pattern as observed in the samples taken from the product tub top. |
| 2 | Acetobacter | No CFU recoveries at/ | No CFU recoveries at/ |

TABLE VI-continued

Summary of Experimental Results:

| Test Sample | Organism | Top of Tub | Bottom of Tub |
|---|---|---|---|
| | aceti | or after day 4. | or after day 4.1 |
| | A. niger | No CFU recoveries at the 4, 7, 14, 28 and 56 day sampling periods. At the 21 day sampling period, however, A. niger was isolated. | Identical CFU recovery pattern as observed in the samples taken from the product tub top. |
| 3 | Acetobacter aceti | CFU recoveries were reduced by 99% on day 4, but the CFU recovered from the sample periods on days 7, 14, 21, and 28 showed a progressive increase in CFU recoveries. By day 56, the CFU recoveries were reduced compared to the previous sampling periods. | Identical recovery pattern as observed in the samples taken from the product tub top. The CFU percent reduction, however, was greater in all time periods than that observed in the samples taken from the tub top. |
| | A. niger | No CFU recoveries were obtained from the sampling periods on days 7, 14, 28 and 56. A. niger was isolated from the sampling periods on day 4 and 21. | Identical CFU recovery pattern as observed in the samples taken from the top of the tubs. |
| Cotton Control | Acetobacter aceti and A. niger | CFU isolated from all the time periods sampled. | |
| Challenge Control | Acetobacter aceti and A. niger | CFU isolated from all the time periods sampled. | |

Therefore, the addition of 0.50% sodium chloride to the preservation composition on either the bioweb (Sample No. 1) or non-bioweb (Sample No. 2) samples showed improved effectiveness then the control (Sample No 3) against *Acetobacter aceti*. The effects of the biocide system against *A. niger* were essentially the same for all the samples tested. It is not believed that because *A. niger* was absent from the samples at 4 days, 7 days, etc., in some of the tests and was present in these same samples at later periods is indicative of *A. niger* regrowth. Rather, the reappearance of *A. niger* is believed to have been due to experimental variability of a slightly longer kill time in some of the individual samples used for testing.

Other embodiments of the invention will be apparent to one skilled in the art from a consideration of the specification or with the practice of the disclosed invention. It is intended that the specification and examples be considered as exemplary only with the true scope and spirit of the invention being indicated by the claims.

What is claimed is:

1. A wet wiper product comprising:
 (a) a fibrous wipe; and
 (b) a hypotonic liquid preservative composition for the wipe comprising:
  (i) water,
  (ii) naturally occurring organic acid in an amount effective to be a preservative, and
  (iii) a naturally occurring salt in an amount effective to increase the efficacy of the naturally occurring organic acid.

2. The wet wiper of claim 1, wherein the organic acid is selected from the group consisting of citric acid, sorbic acid, malic acid, tartaric acid, benzoic acid, and mixtures thereof 3. The wet wiper of claim 1, wherein the organic acid is present in a concentration within the range of about 0.1 to about 0.7 w/v % based upon the liquid preservative composition.

4. The wet wiper of claim 1, wherein the organic acid comprises a mixture of about 0.01 w/v % to about 0.2 w/v % sorbic acid and about 0.1 w/v % to about 0.5 w/v % citric acid based upon the liquid preservative composition.

5. The wet wiper of claim 1, wherein the salt is selected from the group consisting of monobasic or dibasic sodium phosphate, potassium chloride, sodium chloride, and mixtures thereof.

6. The wet wiper of claim 1, wherein the salt is present in a concentration of about 0.1 w/v % to about 0.9 w/v % based upon the liquid preservative composition.

7. The wet wiper of claim 1, wherein the fibrous wipe is an antimicrobially active non-woven web.

8. The wet wiper of claim 1, wherein the liquid preservative composition has an osmotic pressure within the range of about 110 milli-osmole/kg to about 280 milli-osmole/kg.

9. A wet wiper product comprising:
 (a) a fibrous wipe; and
 (b) a liquid preservative composition for the wipe comprising:
  (i) water,
  (ii) a naturally occurring organic acid selected from the group consisting of sorbic acid, citric acid, malic acid, tartaric acid, benzoic acid, and mixtures thereof and present in an amount effective to be a preservative, and
  (iii) a naturally occurring salt selected from the group consisting of monobasic or dibasic sodium phosphate, potassium chloride, sodium chloride, and mixtures thereof, the salt being present in an amount effective to increase the efficacy of the naturally occurring organic acid.

10. The wet wiper of claim 9, wherein the organic acid is present in a concentration of about 0.1 w/v % to about 0.7 w/v % based upon the liquid preservative composition.

11. The wet wiper of claim 10, wherein the organic salt is present in a concentration of about 0.1 w/v % to about 0.9 w/v % based upon the liquid preservative composition.

12. The wet wiper of claim 10, wherein the organic salt is present in a concentration of about 0.1 w/v % to about 0.5 w/v % based upon the liquid preservative composition.

13. The wet wiper of claim 9, wherein the organic acid comprises a mixture of about 0.01 w/v % to about 0.20 w/v % sorbic acid and about 0.1 w/v % to about 0.5 w/v % citric acid based upon the liquid preservative composition.

14. The wet wiper of claim 13, wherein the sorbic acid is present in the range of about 0.05 w/v % to about 0.10 w/v % and the citric acid is present in the range of about 0.3 w/v % to about 0.5 w/v %.

15. The wet wiper of claim 9, wherein the pH of the liquid preservative composition is in the range of about 2.0 to about 3.2.

16. The wet wiper of claim 9, wherein the liquid preservative composition is hypotonic and has an osmotic pressure within the range of about 110 milli-osmole/kg to about 280 milli-osmole/kg.

17. An antimicrobially active wet wiper comprising:
(a) a fibrous wipe, and
(b) a hypotonic liquid preservative composition for the wipe comprising:
  (i) water,
  (ii) a naturally occurring organic acid comprising a mixture of about 0.01 w/v % to about 0.20 w/v % sorbic acid and about 0.1 w/v % to about 0.5 w/v % citric acid based upon the liquid preservative composition, and
  (iii) a naturally occurring salt comprising about 0.1 w/v % to about 0.5 w/v % sodium chloride based upon the liquid preservative composition.

18. The wet wiper of claim 17, wherein the liquid preservative composition has an osmotic pressure within the range of about 110 milli-osmole/kg to about 280 milli-osmole/kg and a pH within the range of about 2.0 to about 3 2.

19. The wet wiper of claim 18, wherein the sorbic acid is present in an amount within the range of about 0.05 w/v % to about 0.10 w/v % and the citric acid is present in the range of about 0.3 w/v % to about 0.5 w/v %, the weight percent ratio of citric acid to sorbic acid being in the range of about 20 to 1 to about 1 to 1.

20. The wet wiper of claim 19, wherein the fibrous wipe is an antimicrobially active non-woven web.

* * * * *